United States Patent [19]
Yamazaki

[11] Patent Number: 5,275,580
[45] Date of Patent: Jan. 4, 1994

[54] AUXILIARY ARTIFICIAL HEART OF THE EMBEDDED-IN-BODY TYPE

[75] Inventor: Kenji Yamazaki, 3-7-15, Honcho, Koganei-shi, Tokyo, Japan

[73] Assignees: Kenji Yamazaki, Tokyo; Sun Medical Technology Research Corporation, Nagano, both of Japan

[21] Appl. No.: 901,826

[22] Filed: Jun. 19, 1992

Related U.S. Application Data

[63] Continuation-in-part of Ser. No. 664,744, Mar. 5, 1991, Pat. No. 5,147,388.

[30] Foreign Application Priority Data

Mar. 8, 1990 [JP] Japan ................................ 2-54910
Jun. 24, 1990 [JP] Japan ............................... 2-164819

[51] Int. Cl.⁵ .............................................. A61M 1/10
[52] U.S. Cl. ............................................ 600/16; 623/3
[58] Field of Search .................... 623/3; 600/16-17, 600/18; 415/900

[56] References Cited

U.S. PATENT DOCUMENTS

| | | | |
|---|---|---|---|
| 3,766,567 | 10/1973 | Kahn et al. | 623/3 |
| 4,955,856 | 9/1990 | Phillips | 600/16 |
| 4,964,864 | 10/1990 | Summers et al. | 623/3 |
| 4,994,078 | 2/1991 | Jarvik | 623/3 |
| 5,147,388 | 9/1992 | Yamazaki | 623/3 |

*Primary Examiner*—Randall L. Green
*Assistant Examiner*—D. Willse
*Attorney, Agent, or Firm*—Nixon & Vanderhye

[57] ABSTRACT

An auxiliary artificial heart embedded in the human body. The auxiliary artificial heart has an apex cordis area ring and a body. The apex cordis area ring is embedded in a cut-out apex cordis area of the human heart. The body includes an elongated pump section and a drive section. The pump section is inserted into one of the ventricles of the human heart, passing through the apex cordis area ring. A front end nozzle whose diameter is smaller than that of the pump section is formed at the front end of the pump section, and it is inserted into the aorta or pulmonary artery, passing through the center of the aorta or pulmonary valve. The pump section sucks blood in the ventricle through its base portion and feeds it into the aorta or pulmonary artery through the front end nozzle.

6 Claims, 8 Drawing Sheets

AUXILIARY ARTIFICIAL HEART OF THE EMBEDDED-IN-BODY TYPE

CROSS-REFERENCE TO THE RELATED APPLICATIONS

This application is a continuation-in-part of U.S. patent application Ser. No. 664,744, filed on Mar. 5, 1991, now U.S. Pat. No. 5,147,388.

BACKGROUND OF THE INVENTION

1. Field of the Invention

The present invention relates to an auxiliary artificial heart of the embedded-in-body type embedded in the left or right ventricle of the heart of a human body.

More particularly, it relates to an auxiliary artificial heart intended to feed blood by a pump in addition to blood fed by the human heart, without damaging the function of the human heart.

2. Description of the Related Art

The conventional artificial hearts of the embedded-in-body type include those of the diaphragm, sack, centrifugal, pusher plate and other systems.

However, these artificial hearts are intended to feed blood, using the human heart as a bypass or instead of the human heart. They are therefore large in size and not suitable for embodiment in the human body. When the artificial heart is large in size, the patient who has the artificial heart embedded in his or her heart must bear a large burden. In addition, that area of the artificial heart which is contacted with blood becomes large, thereby causing a thrombus.

Further, it is required that the artificial heart is durable and reliable. Conventional artificial hearts are complicated in structure and they have a limitation in enhancing their durability and reliability.

In addition to these artificial hearts intended to feed blood, using the human heart as a bypass or instead of the human heart, there is another artificial heart of such a type as disclosed in an essay "In Vivo Evaluation Of A Peripheral Vascular Access Axial Flow Blood Pump" reported by Richard K. Wampler et al on pages 450–454 of "TRANS AM SOC ARTIF INTERN ORGANS" Vol. XXXIV (1988).

This artificial heart has a small-sized pump inserted into the artery and a tube is attached to a sucking opening of the pump. The tube is inserted into the ventricle of the human heart, passing through the artery valve. Blood in the ventricle is sucked through the tube and fed into the artery. This artificial heart does not substantially damage the function of the human heart and it can feed blood in addition to blood fed by the human heart.

The pump must be small in size to insert it into the artery. To meet this requirement, the pump in the above-mentioned artificial heart excludes a driving motor from it. The driving motor is arranged external of the human body, and the driving force is supplied from the motor through a wire to it. Due to such an arrangement, not only the movement of the patient is restricted while the artificial heart is operating, but also the patient cannot carry the artificial heat for a long time.

SUMMARY OF THE INVENTION

A first object of the present invention is to provide an auxiliary artificial heart capable of feeding blood into the artery by a pump in addition to blood fed by the human heart without damaging the function of the human heart and disturbing the flow of blood in the artery.

Another object of the present invention is to provide an artificial heart small in size and light in weight.

A further object of the present invention is to provide an artificial heart which is durable and reliable.

These and other objects as well as merits of the present invention can be achieved by the following examples of the artificial hearts according to the present invention.

An example of the artificial heart according to the present invention has an apex cordis area ring embedded in a cut-out apex cordis area of the human heart, and an artificial heart body. The apex cordis area ring is embedded in that area of the apex cordis of the human heart which has been surgically removed. The body is inserted into one of the ventricles of the human heart, passing through the apex cordis area ring.

The body comprises a pump section and a drive section for driving the pump section. The pump section is shaped like a cylinder and it has a front end nozzle, whose diameter is smaller than its diameter, at its front end. It is inserted into the right or left ventricle of the human heart, passing through the apex cordis area ring. The drive section is preferably located outside the human heart. The front end nozzle is inserted into the aorta or pulmonary artery, passing through the center of the aorta or pulmonary valve.

The pump section is driven by a motor in the drive section to such blood in the ventricle through the base portion thereof and fed it into the aorta or pulmonary artery through the front end nozzle. The front end nozzle has a relatively small diameter. Even when it is inserted into the aorta or pulmonary artery, passing through the aorta or pulmonary valve, therefore, it does not substantially damage the aorta or pulmonary valve.

This artificial heart can feed blood in the ventricle into the aorta or pulmonary artery without adding any influence to the function of the human heart, as described above. This enables a sufficient amount of blood to be fed into the aorta or pulmonary artery by the artificial heart as well as by the beating human heart. Further, the body of the auxiliary artificial heart is inserted into the ventricle and only a part of the front nozzle is inserted into the artery. This prevents the flow of blood in the artery from being disturbed by the artificial heart. According to this example of the artificial heart of the present invention, the drive section which includes a motor and the like is located outside the human heart and it is only the pump section that is inserted into the ventricle. The volume of this pump section can be made relatively small or smaller than that of the ventricle obtained when it shrinks to the greatest extent. Therefore, the natural function of the human heart cannot be damaged by this pump section. Furthermore, the artificial heart adds no influence to the natural function of the human heart, as described above, even if it should get out of order. The amount of blood fed by the beating human heart can be thus still guaranteed, thereby preventing the occurrence of sudden death.

According to this example of the artificial heart, the pump section includes a screw pump of the axial-flow type. This screw pump can be made simple in construction and small in size while providing high durability and reliability.

According to this example of the artificial heart, the drive section is controlled by a control means, depending upon the state of the human heart or the number of its beats, the blood pressure in it and the like, so as to effectively assist its function.

According to another example of the artificial heart of the present invention, the front end nozzle is tilted relative to the pump section to match an angle which is formed by the axial direction of the ventricle and that of the artery. Further, the front end of the front end nozzle is held in the center of the artery or artery valve by a positioning ring. The front end nozzle is thus held at a predetermined position relative to the artery valve not to add any influence to the function of the artery valve.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
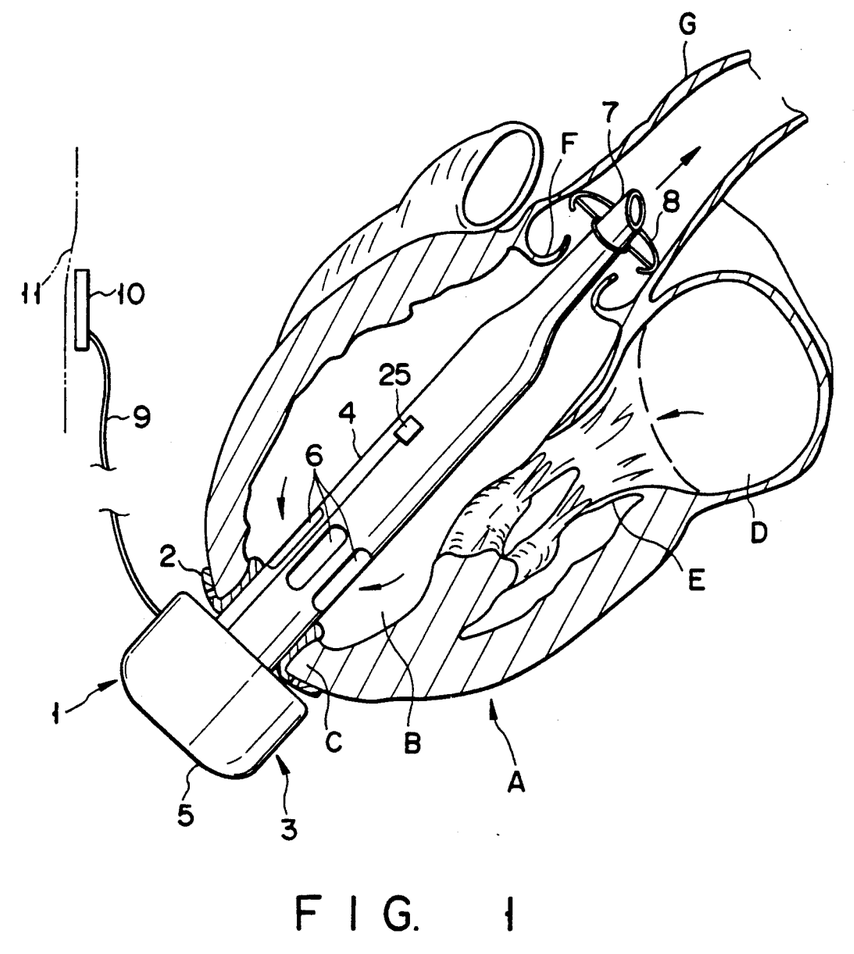
FIG. 1 shows the whole of a first example of the artificial heart according to the present invention embedded in the left ventricle of the human heart.

FIGS. 1 through 5 show a first example of the artificial heart according to the present invention. FIG. 1 shows the artificial heart of the present invention embedded in the left ventricle B of the heart A of the human body. Capital letter C denotes an apex cordis area, D a left atrium, E a mitral valve, F an aorta valve and G an aorta.

This artificial heart 1 comprises an apex cordis area ring 2 and an artificial heart body 3.

The apex cordis area ring 2 is a short cylinder provided with a collar and it is fitted into the excised apex cordis area C of the heart A, passing through this area C.

The artificial heart body 3 comprises a pump section 4 and a drive section 5 for driving the pump section 4. The pump section 4 is a relatively small-sized cylinder, in which a smaller-sized pump of the axial-flow type is housed. The pump section 4 has a nozzle 7, which has a smaller diameter, at the front thereof. The pump section 4 is inserted into the left ventricle B, passing through the apex cordis area ring 2. The pump section 4 is sealed relative to the apex cordis area ring 2 by a well-known seal means to prevent blood from leaking outside. The front end nozzle 7 of the pump section 4 is inserted into the aorta G, passing through the center of the aorta valve F. The drive section 5 is preferably embedded in the human body outside the heart A, as seen in the case of this example.

A positioning ring 8 is fitted onto the front end of the front end nozzle 7. The positioning ring 8 is located in the aorta G and serves to position the front end nozzle 7 at the center of the aorta G or aorta valve F and hold it there.

A motor, a control means, a battery and the like are housed in the drive section 5, which is connected to an electrode 10 of the non-contact type through a line 9, and the electrode 10 is embedded in the human body near the skin H thereof.

According to the artificial heart 1 arranged as described above, the pump section 4 is driven by the drive section 5 to suck blood in the left ventricle B through plural slits 6 at the base thereof and pressure-feed it into the aorta G through the front end nozzle 7.

The volume of the pump section 4 is relatively small and smaller than that of the left ventricle B obtained when it is shrunk to the greatest extent. Even when the pump section 4 is inserted into it, therefore, the pump section 4 adds no influence to it. Further, the front end nozzle 7 is small in diameter and passes through the center of the aorta valve F. This prevents the front end nozzle 7 from adding any influence to the function of the aorta valve F. Assisting the function of the heart A of the human body without adding any influence to it, therefore, this artificial heart feeds blood in addition to that blood which is fed by the heart of the human body to thereby keep the amount of blood enough to be fed into the aorta G.

Figure 2:
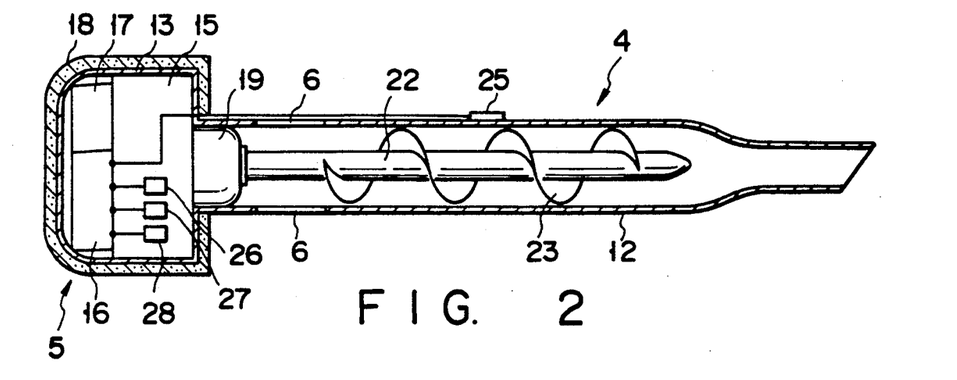
FIG. 2 is a vertically-sectioned view showing the artificial heart.

The arrangement and operation of the artificial heart body 3 will be described in more detail with reference to FIGS. 1 and 2.

The pump section 4 has a cylindrical metal casing 12 and the drive section 5 also has a metal casing 13. A motor 15 is housed in the drive section 5. DC, ultrasonic and other motors can be used as the motor 15. A small-sized screw pump 21 of the axial-flow type is housed in the pump section 4. The screw pump 21 comprises a shaft 22 and a vane 23 and it is of the single spiral type. The shaft 22 is supported by a bearing 19 and connected to the motor 15.

The casings 12 and 13 of the pump and drive sections 4 and 5 are welded to each other or made as a single unit, so that the heat of the casing 13 of the drive section 5 can be transmitted to the casing 12 of the pump section 4 through heat conduction. Therefore, heat created by the motor 15 is transmitted to the casing 12 of the pump section 4 through the casing 13 and radiated from the casing 12 into blood. The temperature of the drive section 5 can be thus prevented from rising. Further, the drive section 5 is covered by heat-insulating material 18. This can prevent the anatomy of that area of the human body in which the drive section 5 is embedded from being broken or burnt at low temperature by the heat created by the motor 15.

According to this example of the artificial heart, a control means 16 and a power battery 17 are housed in the drive section 5. The power battery 17 is connected to the terminal 10 and regularly charged by a charger (not shown) which is electromagnetically connected to the terminal 10 through the skin H of the human body.

According to this example, the control means 16 controls the artificial heart variously. Namely, a pressure detector 25 of the thin type is attached to the outer circumference of the pump section 4, for example. Further, a detector 26 for detecting the number of rotations of the motor 15, a temperature detector 27, a humor detector 28 for detecting humors such as blood entered into the drive section 5, and the like are housed in the drive section 5. Signals are sent from these detectors to the control means 16, which responds to these signals to add various kinds of controls to the artificial heart according to a program previously stored.

For example, the number of heartbeats of the human heart A is detected responding to the changing signal which is applied from the pressure detector 25 to denote the pressure in the left ventricle. The number of rotations of the motor 15 is changed responsive to the number of heartbeats thus detected, so that the amount of blood fed into the aorta through the artificial heart can be changed responsive to the number of heartbeats of the human heart.

Further, when the shrinking force of the left ventricle B of the human heart A lowers to thereby reduce the amount of blood fed into the aorta through the left ventricle B itself, the pressure in the left ventricle B which expands to the greatest extent rises. Therefore, this state of the left ventricle B is detected by the pressure detector 25 and the number of rotations of the motor 15 is increased so as to compensate for the reduction of blood which is fed into the aorta through the left ventricle B of the human heart A. As the result, the amount of blood fed can be kept at such a level as needed.

Furthermore, in a case where the temperature of the motor 15 rises to an abnormal value or the casing 13 of the drive section 5 or the seal of the bearing 19 is damaged to allow humors such as blood to enter into the drive section 5, this state is ascertained in response to the signal applied from the temperature or humor detector 27 or 28. An alarm signal responsive to the occurrence of abnormality can be provided, e.g., sounding a buzzer, flickering or vibrating a lamp or sending electromagnetic alarm signal to the external control means.

Figure 3:
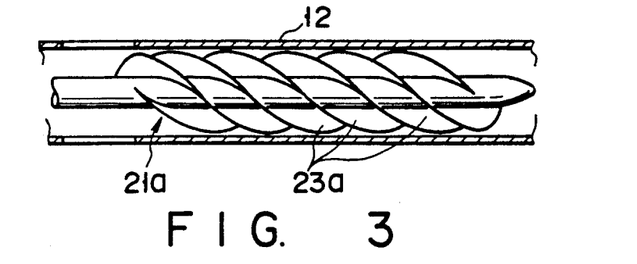
FIG. 3 is a vertically-sectioned view showing a variation of the screw pump.
Figure 4:
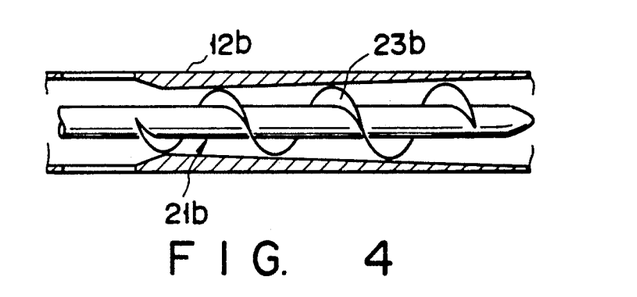
FIG. 4 is a vertically-sectioned view showing another variation of the screw pump.
Figure 5:
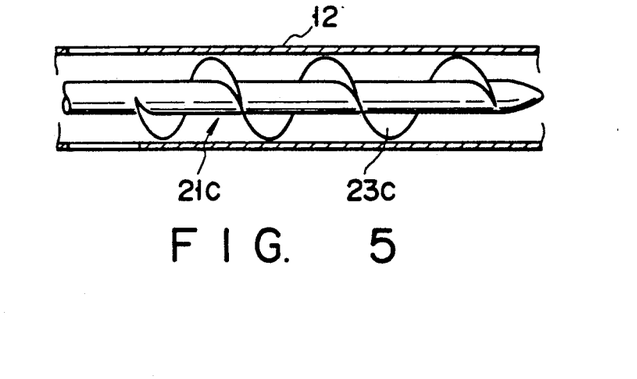
FIG. 5 is a vertically-sectioned view showing a further variation of the screw pump.
Figure 6:
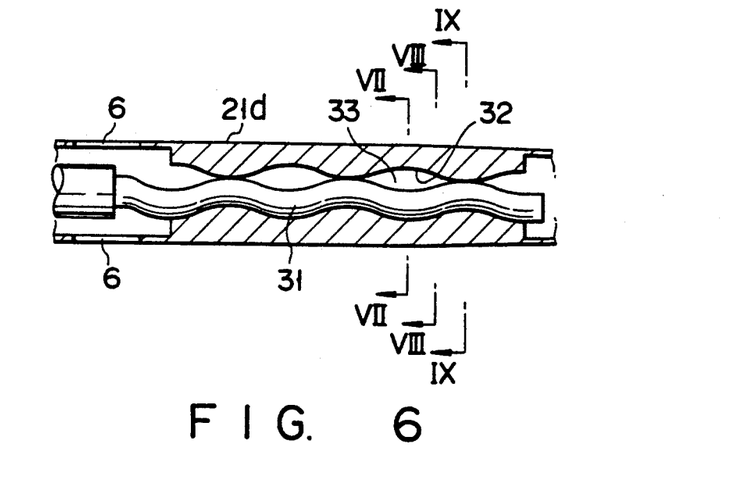
FIG. 6 is a vertically-sectioned view showing the pump section of a second example of the artificial heart according to the present invention.

FIGS. 3 through 5 show various kinds of screw pumps employed by the first example of the artificial heart 1.

As described above, the artificial heart of the present invention is intended to insert its pump section 4 into the left ventricle B of the human heart A. It is therefore preferable that the pump section 4 has a volume smaller than that of the left ventricle B obtained when this left ventricle B shrinks to the greatest extent. This can be satisfactorily realized even by the screw pump 21 shown in FIG. 2 and provided with the single vane 23. However, it is preferable that the volume of the pump section 4 is made as small as possible because the pump section 4 is inserted into the heart of the human body. In order to make the pump section 4 smaller-sized, therefore, it is necessary that the screw pump is made higher in speed and efficiency.

To meet these needs, a screw pump 21a shown in FIG. 3 is arranged to have three sheets of vanes 23a which are attached about the shaft 22 in a triple spiral. This screw pump 21a can be made smaller in size but larger in capacity.

According to another screw pump 21b shown in FIG. 4, the outer diameter of a circle drawn by its vane 23b becomes larger as it come nearer to its front end. The inner diameter of a casing 12b is naturally tapered in this case to house the vane 23b therein. In the case of the screw pump 21b, the distribution of pressure in the casing 12b can be made uniform in the axial direction of the casing 12b and the occurrence of cavitation on both sides of the vane 23b can be prevented. The screw pump 21b can be thus made higher in speed.

According to a further screw pump 21c shown in FIG. 5, the pitch of a vane 23c is made larger as it comes nearer to its front end. In the case of the screw pump 21c, the occurrence of cavitation can also be prevented as seen in FIG. 4. This enables the screw pump 21c to be made higher in speed.

The screw pump may be a combination of those shown in FIGS. 3 through 5. For example, its outer diameter and pitch may be made larger as it comes nearer to its front end, as shown in FIGS. 4 and 5.

The pump section 4 may not necessarily be provided with the one of those screw pumps which are shown above in the case of the present invention.

Figure 7:
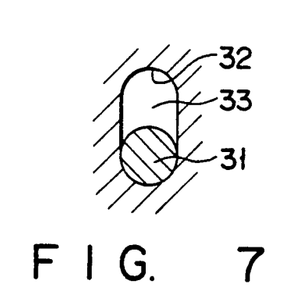
FIG. 7 is a sectional view taken along a line VII—VII in FIG. 6.
Figure 8:
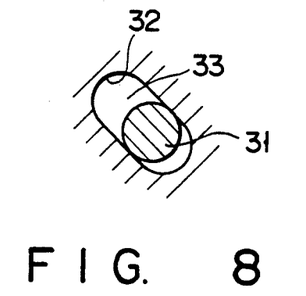
FIG. 8 is a sectional view taken along a line VIII—VIII in FIG. 6.
Figure 9:
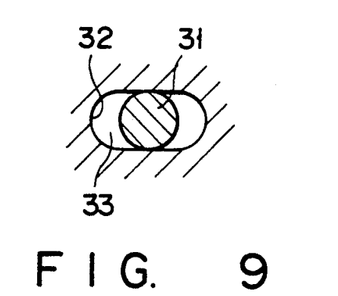
FIG. 9 is a sectional view taken along a line IX—IX in FIG. 6.

For example, FIGS. 6 through 9 show a second example of the artificial heart according to the present invention, in which the pump section 4 houses therein a single screw pump of the eccentric type. A screw groove 32 having an elliptic section is formed in a casing 12d and a rotor 31 of the spiral type having a circular section is fitted into the screw groove 32. When rotated, the rotor 31 reciprocates while sliding in the screw groove 32 and a space 33 formed by the rotor 31 and the inner face of the screw groove 32 is successively moved to the front end of the screw section 4 in the axial direction thereof, as shown in FIGS. 7 through 9, to thereby feed blood into the aorta. The pump of this type creates no pulse while it is under operation.

Figure 10:
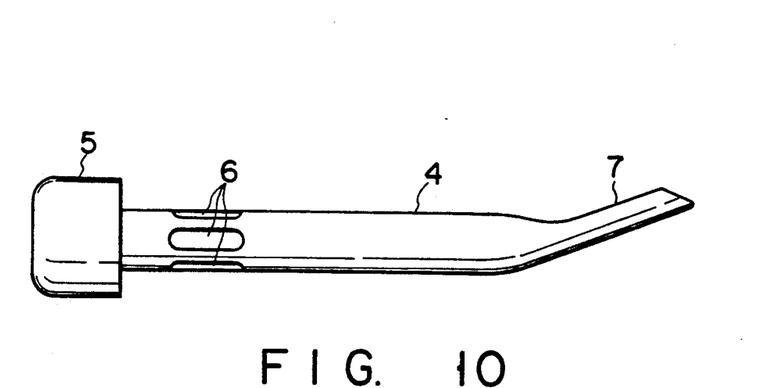
FIG. 10 is a side view showing a third example of the artificial heart according to the present invention.

FIG. 10 shows a third example of the artificial heart according to the present invention, in which the front end nozzle 7 is tilted relative to the center line of the pump section 4.

Axial center lines of the left ventricle B, of the aorta valve F and of the aorta G of the human heart are usually aligned with one another. It may be therefore arranged in this case that the pump section 4 and the front end nozzle 7 are on a same axial center line. Depending upon the person who uses the artificial heart, particularly in the case where the person is old, one of the axial center lines of the left ventricle and of the aorta is sometimes tilted relative to the other at an angle. When the front end nozzle 7 is tilted relative to the pump section 4 at this angle in this case, as shown in FIG. 10, it can be accurately positioned in the centers of the aortas and of the aorta valve not to damage the function of the aorta valve.

Although description has been made of the case where the artificial heart is inserted into the left ventricle of the human heart, the artificial heart may be inserted into the right ventricle thereof.

Figure 11:
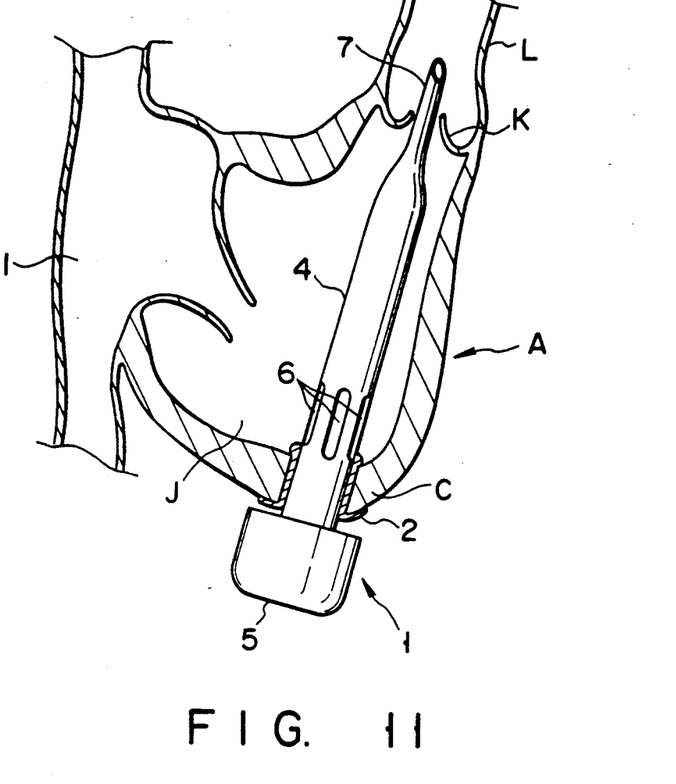
FIG. 11 shows the artificial heart of the present invention embedded in the right ventricle of the human heart.

FIG. 11 shows the artificial heart inserted into the right ventricle J of the human heart A. In FIG. 11, capital letter I represents the right atrium, K the pulmonary valve, and L the pulmonary artery. Needless to say, dimension, shape and others of the pump section 4 of the artificial heart are designed in this case to match those of the right ventricle J, pulmonary valve K and pulmonary artery L.

Figure 12:
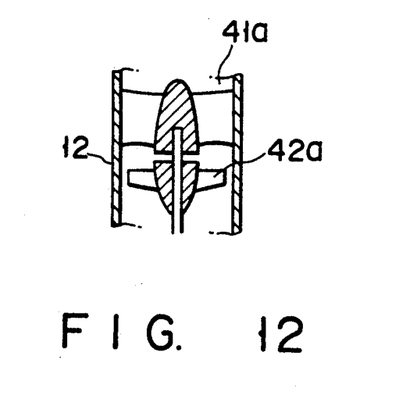
FIG. 12 is a vertically-sectioned view showing a part of the pump section of a fourth example of the artificial heart according to the present invention.
Figure 13:
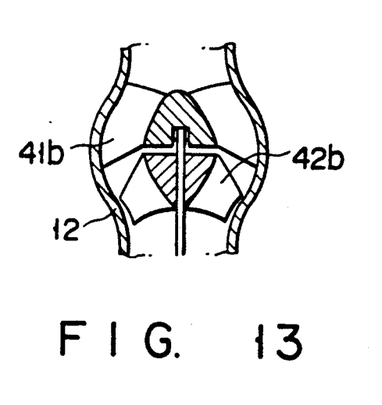
FIG. 13 is a vertically-sectioned view showing a part of variation of the pump section.

FIGS. 12 and 13 show a third example of the artificial heart according to the present invention, in which an axial-flow pump of the propeller type is housed in the pump section 4.

In FIG. 12, reference numeral 41a denotes a stator vane and 42a propellers.

In the case of the axial-flow pump shown in FIG. 13, that portion of the casing 12 which corresponds to propellers is made larger in diameter. Reference numeral 41b represents a stator vane and 42b propellers.

The arrangement of each of the above-described examples according to the present invention may be changed to have other various functions needed as the artificial heart. The control means, the power battery and the like may be located outside the human body, for example. Further, it is preferable from the viewpoint of radiation that the casing of the pump section and the screw pump housed in the pump section are made of metal. When they are made of metal, heparin coating is applied to their parts which are contacted with blood so as to make them antithrombogenic. Coating of polyurethane, pyritocarbon or the like, for example, is vapor-deposited on them.

The artificial heart is embedded in the human body. If necessary, therefore, it may be arranged that some of its parts are made by a soft material as not to damage the organ of the human body. For example, the front end nozzle of the pump section may be made from a by soft material such as polyurethane so as to more effectively prevent the aorta valve from being damaged.

Figure 14:
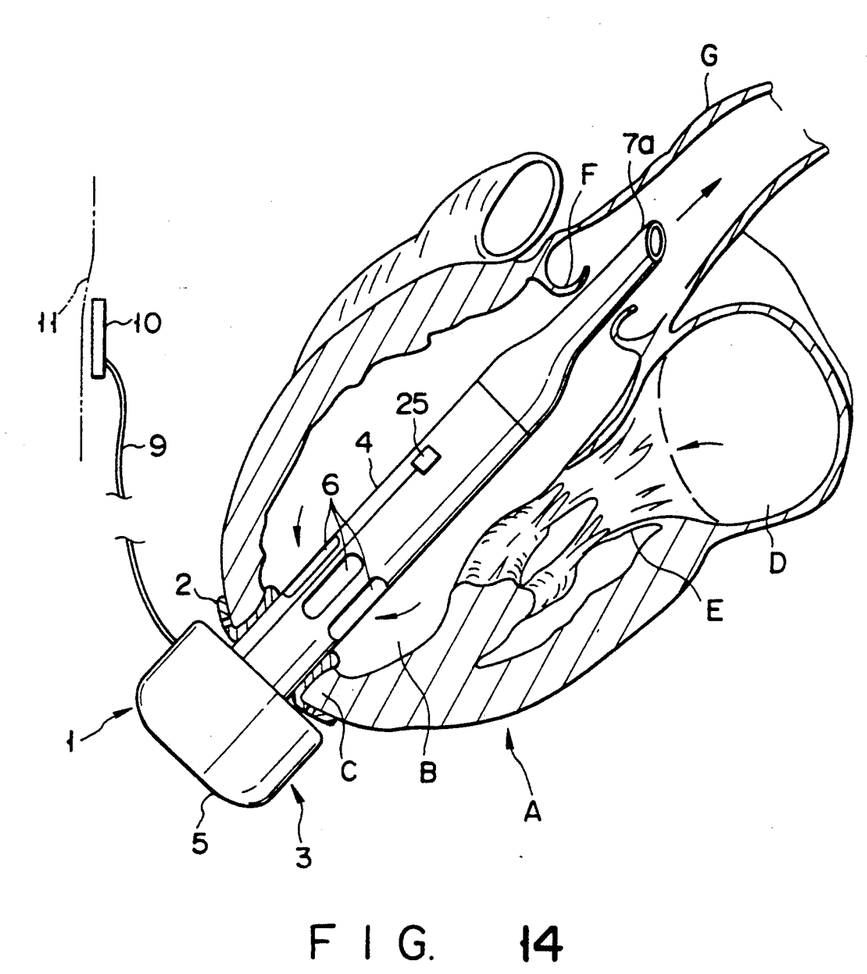
FIG. 14 is a view, showing a case where an auxiliary artificial heart according to a fifth embodiment of the invention is inserted in the left ventricle of the human heart.

FIG. 14 shows an auxiliary artificial heart according to a fifth embodiment. This auxiliary artificial heart has a front end nozzle made of an elastic material. The casing 12 of a pump section 4 is made of a metal and formed cylindrical as in the aforementioned embodiments. A front end nozzle 7a is attached to an end portion of the casing 12. The nozzle 7a has a shape similar to that of the nozzles in those embodiments, but is made of an elastic material such as polytetrafluoroethylene, polyurethane, or a silicone resin. Accordingly, the nozzle 7a is flexible.

Figure 15:
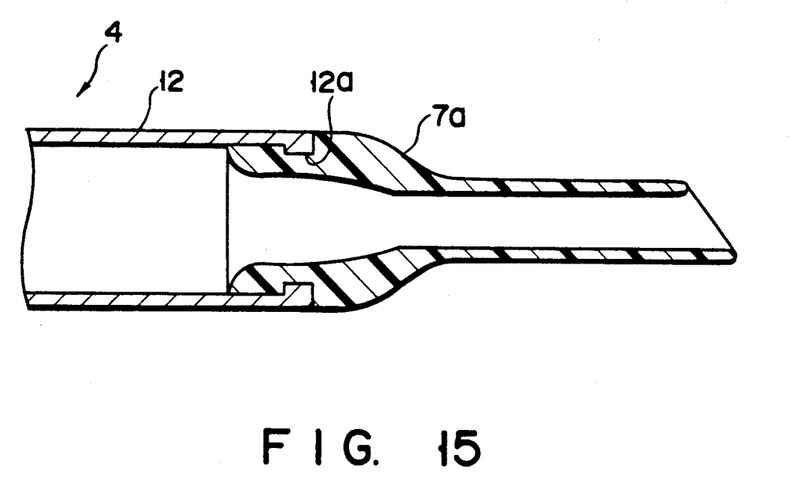
FIG. 15 is a longitudinal sectional view of a front end nozzle portion shown in FIG. 14.

FIG. 15 shows an example of the attachment structure of the front end nozzle 7a. An annular projection 12a is formed on the inner periphery of the end portion of the casing 12 of the pump section 4. An end portion of the nozzle 7a is fitted in the casing 12 with the annular projection 12a engaged therewith. There are no stepped portions between the outer periphery of the casing 12 and that of the nozzle 7a, i.e., they are smoothly connected to each other.

Since the front end nozzle 7a employed in the fifth embodiment has flexibility, it does not hurt the aorta valve F. Further, when the pump section 4 is inclined, the nozzle 7a is elastically bent, thereby reducing the load applied to the aorta valve F. Thus, the use of the aforementioned positioning ring 8 can be omitted. In a case where the positioning ring 8 is not employed, a predetermined portion of the front end nozzle 7a may be secured to the aorta valve F or the like by means of a thread, so as to prevent the nozzle 7a from being excessively biased in position.

Figure 16:
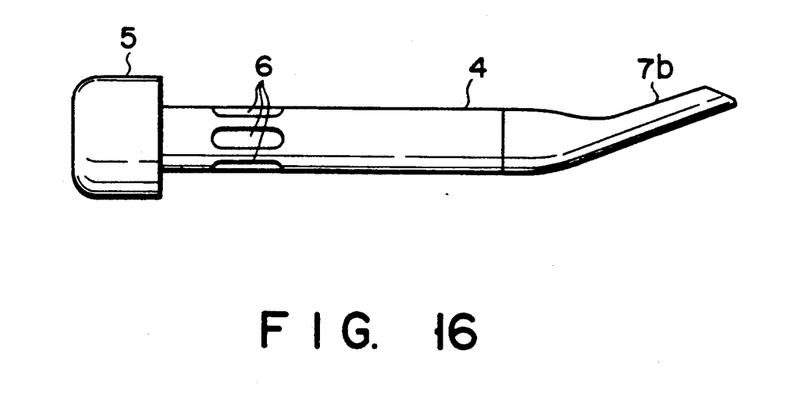
FIG. 16 is a side view of an auxiliary artificial heart according to a sixth embodiment of the invention.

Moreover, also in the case of forming the nozzle of an elastic material, it may have a bent portion 7b so as to be mated with the shape and/or angle of the heart and aorta, as in a sixth embodiment shown in FIG. 16.

Furthermore, if pressure in the human heart becomes lower than that in the aorta owing to stop of the auxiliary artificial heart or other reason, it is possible that blood in the aorta G is returned into the left ventricle B through the artificial heart. To avoid this, a non-return valve 50a may be provided at an end seventh embodiment shown in FIGS. 17A-18B.

Figure 17A:
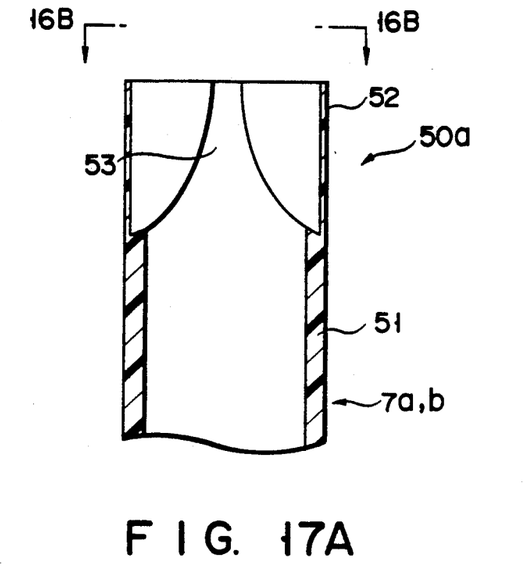
FIG. 17A is a longitudinal sectional view of a non-return valve provided at the front end nozzle portion, according to a seventh embodiment of the invention.
Figure 17B:
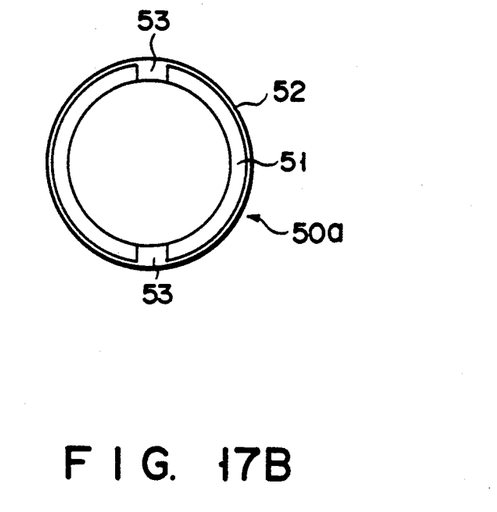
FIG. 17B shows the non-return valve as viewed from the direction indicated by the arrows 17B in FIG. 17A.

Specifically, the end portion of the nozzle 7a or 7b has a thick portion 51, and a cylindrical thin portion 52 extending from a end of the thick portion 51. A pair of projections 53 extend to the end of the thin portion 52. The projections 53 have opposite sides tapered smoothly.

The thin and thick portions 52 and 51 may be formed of polyurethane integrally as one piece. Alternatively, they may be made of different materials, e.g., the thick portion 51 is made of polyurethane, and the thin portion 52 polytetrafluoroethylene, and they may be secured to each other in an appropriate manner.

Figure 18A:
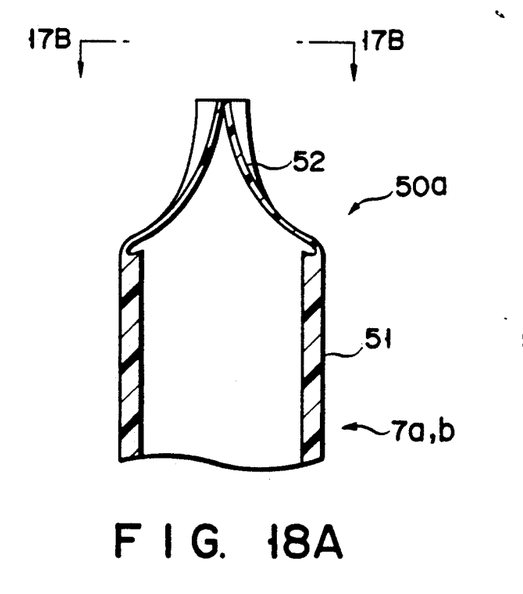
FIG. 18A is a longitudinal sectional view of the non-return valve in FIG. 17A, showing its closed state.
Figure 18B:
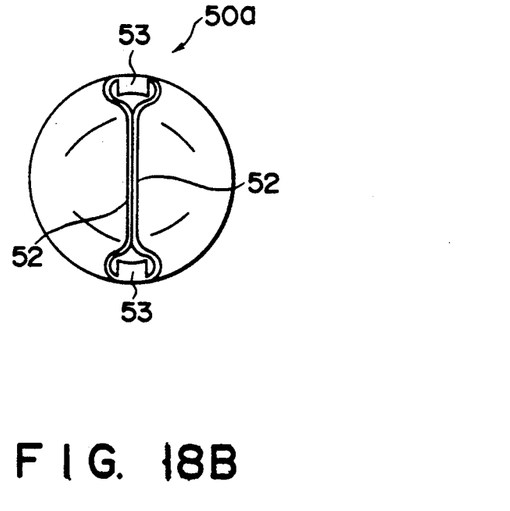
FIG. 18B shows the non-return valve as viewed from the direction indicated by the arrows 18B in FIG. 18A.

When the artificial heart according to the seventh embodiment is operated to discharge blood from the front end nozzles 7a and 7b, the thin portion 52 expands to become cylindrical as shown in FIGS. 17A and 17B, thereby allowing blood flowing therethrough. On the other hand, if pressure in the pump section 4 becomes lower than that in the aorta G owing to stop of the auxiliary artificial heart or other reason, this pressure difference causes the thin portion 52 to contract and close its end portion as shown in FIGS. 18A and 18B, thereby preventing return of blood.

Figure 19:
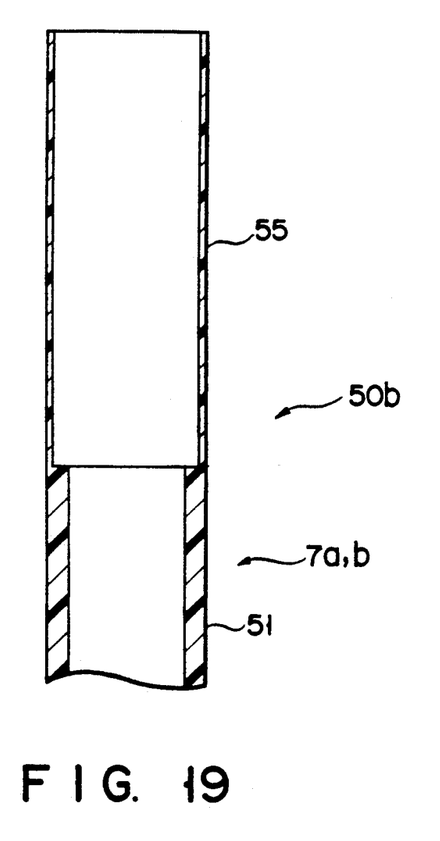
FIG. 19 is a longitudinal sectional view of a non-return valve provided at the front end nozzle portion, according to an eighth embodiment of the invention.
Figure 20:
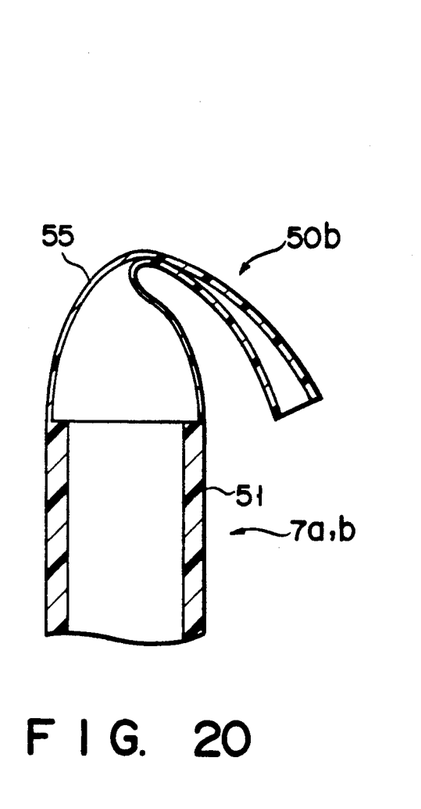
FIG. 20 is a longitudinal sectional view of the non-return valve in FIG. 19, showing its closed state.

Further, this non-return valve may be constructed as shown in FIGS. 19 and 20 directed to an eighth embodiment. A non-return valve 50b according to the eighth embodiment comprises a thick portion 51 and a long cylindrical thin portion 55 extending from an end of the thick portion, and has no projections similar to those 53 employed in the seventh embodiment.

When the artificial heart according to the eighth embodiment is operated to discharge blood from the front end nozzles 7a and 7b, the thin portion 55 expands to become cylindrical as shown in FIG. 19, thereby allowing blood flowing therethrough. On the other hand, if pressure in the pump section 4 becomes lower than that in the aorta G owing to stop of the auxiliary artificial heart or other reason, this pressure difference causes the thin portion 55 to be bent as shown in FIG. 20, thereby closing the portion 55 and preventing return of blood.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An auxiliary artificial heart of the embedded-in-body type structured to be embedded in one of the ventricles of the heart of a human body comprising:

a) an apex cordis area ring structured to be fixedly embedded in a cutout portion of the apex cordis area of the human heart;

b) an artificial heart body including a pump section, a drive section for driving the pump section, and a nozzle;

said pump section including a cylindrical pump of the axial-flow type having a base portion and a front end, driven by the drive section to suck blood through the base portion of the pump section and discharge it through the front end thereof, and said pump section being structured to be inserted into one of the ventricles, passing through the apex cordis area ring, said pump section defining a volume smaller than that of the ventricle in the human heart obtained when it naturally shrinks to the greatest extent; and said pump section having a casing, and said nozzle being formed of a flexible material differing from that of said casing, said drive section being structured to be arranged outside the human heart;

said nozzle being provided at the front end of the pump section and structured to be inserted through the aortic valve of the human heart and into the aorta, whereby the blood in the ventricle is fed into the aorta through the nozzle at the front end of the pump by means of the pump section.

2. The auxiliary artificial heart of the embedded-in-body type according to claim 1, wherein said front end nozzle has a non-return valve for preventing blood from returning to the pump section through the nozzle.

3. The auxiliary artificial heart of the embedded-in-body type according to claim 1, wherein said pump section includes a pump of the screw type.

4. The auxiliary artificial heart of the embedded-in-body type according to claim 1, wherein said front end nozzle is tilted relative to the pump section so as to match an angle which is formed by the axial direction of that ventricle of the human heart in which the artificial heart is embedded and the axial direction of the aorta.

5. The auxiliary artificial heart of the embedded-in-body type according to claim 1, including a control means, said drive section being connected to said control means, said control means being operable to control the operation of the drive section, depending upon the state of the heart in the human body.

6. The auxiliary artificial heart of the embedded-in-body type according to claim 5, wherein said control means is housed in the drive section.

* * * * *